US010981735B2

(12) United States Patent
Koizumi et al.

(10) Patent No.: US 10,981,735 B2
(45) Date of Patent: Apr. 20, 2021

(54) PNEUMATIC CONVEYANCE METHOD FOR METHIONINE

(71) Applicant: SUMITOMO CHEMICAL COMPANY, LIMITED, Tokyo (JP)

(72) Inventors: Yoshiyuki Koizumi, Niihama (JP); Naoya Yamashiro, Niihama (JP); Rikuri Uejima, Niihama (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 12 days.

(21) Appl. No.: 16/613,481

(22) PCT Filed: May 15, 2018

(86) PCT No.: PCT/JP2018/018669
§ 371 (c)(1),
(2) Date: Nov. 14, 2019

(87) PCT Pub. No.: WO2018/212149
PCT Pub. Date: Nov. 22, 2018

(65) Prior Publication Data
US 2021/0087000 A1    Mar. 25, 2021

(30) Foreign Application Priority Data

May 16, 2017 (JP) .............................. JP2017-096909

(51) Int. Cl.
*B65G 53/66* (2006.01)
*B65G 53/04* (2006.01)

(52) U.S. Cl.
CPC ........ *B65G 53/04* (2013.01); *B65G 2812/165* (2013.01)

(58) Field of Classification Search
CPC .. B65G 53/04; B65G 53/66; B65G 2812/165; C07C 319/26; C07C 319/28; C07C 323/57; C07C 323/58
(Continued)

(56) References Cited

U.S. PATENT DOCUMENTS 6,261,338 B1    7/2001  Mahoney et al.
6,310,240 B1 *  10/2001 Contractor .............. C07C 51/16
                                              562/535
(Continued)

FOREIGN PATENT DOCUMENTS

CN    1291528 A      4/2001
JP    60-152451 A    8/1985
(Continued)

OTHER PUBLICATIONS

International Search Report for International Application No. PCT/JP2018/018669, dated Jun. 26, 2018.
(Continued)

*Primary Examiner* — Joseph A Dillon, Jr.
(74) *Attorney, Agent, or Firm* — Birch, Stewart, Kolasch & Birch, LLP

(57) ABSTRACT

The present invention provides a method of airflow transportation of methionine that can minimize the crushing of methionine, which is characterized in that when methionine is transported as airflow using carrier gas, the flow state of methionine is a low concentration floating flow type, and the mixing ratio of methionine and carrier gas is in the range of 4 to 10 kg-methionine/kg-carrier gas. In the method of airflow transportation of methionine of the present invention, if the D50 of methionine is in the range of 150 to 425 µm, the increase rate of the fine powder can be suppressed to 1.5% or less by maintaining the mixing ratio at 4 to 10 kg-methionine/kg-carrier gas, and can be suppressed to 1%

(Continued)

or less by maintaining the mixing ratio at 5 to 10 kg-methionine/kg-carrier gas.

4 Claims, 2 Drawing Sheets

(58) Field of Classification Search
USPC .......... 406/12, 19, 197; 562/534, 535, 599; 568/486
See application file for complete search history.

(56) References Cited

U.S. PATENT DOCUMENTS

| | | |
|---|---|---|
| 8,217,197 B2 | 7/2012 | Koizumi et al. |
| 2002/0155541 A1* | 10/2002 | Naughton .............. C12M 41/32 435/69.1 |
| 2009/0171117 A1* | 7/2009 | Arnold ................. C07C 51/252 562/534 |
| 2011/0028760 A1 | 2/2011 | Dubois et al. |
| 2011/0319659 A1* | 12/2011 | Yoshikawa ........... C07C 319/20 562/559 |
| 2013/0274508 A1* | 10/2013 | DeCourcy ............... B01J 8/065 562/534 |
| 2015/0361457 A1* | 12/2015 | Medoff ................. B65G 27/00 435/141 |
| 2015/0368684 A1* | 12/2015 | Medoff ................... C10L 1/023 435/99 |
| 2018/0043281 A1* | 2/2018 | Chen .................... B01D 9/0054 |

FOREIGN PATENT DOCUMENTS

| | | |
|---|---|---|
| JP | 11-79394 A | 3/1999 |
| JP | 2004-43102 A | 2/2004 |
| JP | 2010-111641 A | 5/2010 |
| WO | WO 2013/005838 A1 | 1/2013 |

OTHER PUBLICATIONS

Kogyo Chosakai Publishing Co., Ltd., Separate volumes of "chemical equipment": Basic knowledge on powder technique, Sep. 9, 1997, pp. 84-86, with its English translation, 16 pages total.

Written Opinion of the International Searching Authority for PCT/JP2018/018669, dated Jun. 26, 2018.

Singaporean Written Opinion dated Oct. 13, 2020 for Application No. 11201910726S.

Chinese Notification of the First Office Action and Search Report (including an English translation thereof) issued in the corresponding Chinese Patent Application No. 201880032156.4 dated Dec. 21, 2020.

Extended European Search Report (ESSR) issued in the corresponding European Application No. 18801578.8, dated Jan. 26, 2021.

* cited by examiner

[Fig. 1]
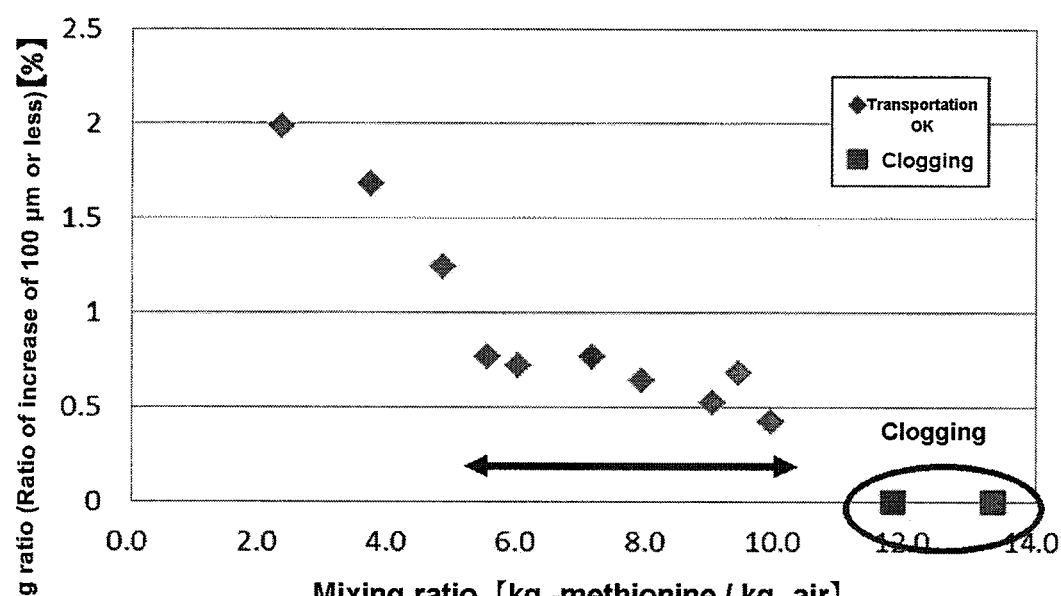

[Fig. 2]
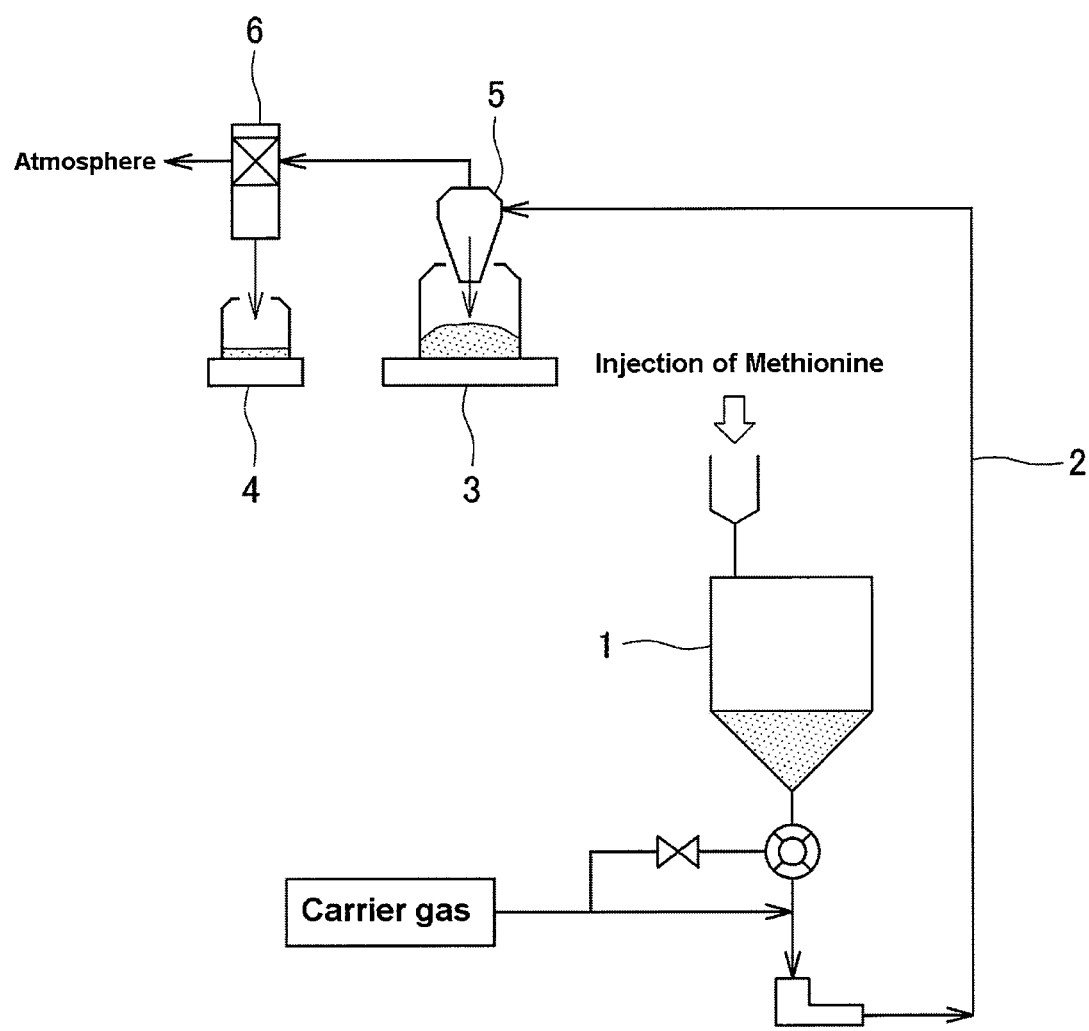

PNEUMATIC CONVEYANCE METHOD FOR METHIONINE

TECHNICAL FIELD

This application claims priority to and the benefit of Japanese Patent Application No. 2017-096909 filed May 16, 2017, the entire contents of which are incorporated herein by reference.

The present invention relates to a method for transporting airflow of methionine.

BACKGROUND ART

Methionine produced through such methionine production process as shown in Patent Document 1 is a powder or a granule, which required transport from the end unit of the manufacturing process to a storage unit such as a tank and further to a filling unit in which methionine is weighed and filled in the container to accomplish its product package.

Airflow transportation with a carrier gas in the pipe is preferable for transportation within the manufacturing apparatus because it is easy to avoid problems of scattering and contamination, but suitable conditions for airflow transportation have been unknown because there is no literature referring to airflow transportation of methionine.

CITATION LIST

Patent Document

Patent Document 1: JP 2010-111641 A

SUMMARY OF THE INVENTION

Problems to be Solved by Invention

While the produced methionine is transported by airflow in the pipe, the methionine is crushed by collision with the lower part of the pipe or the bent pipe part, etc., thereby reduced handleability because of clogging of valves etc., provided in pipes caused by powdering, and product quality of methionine itself is lowered due to increase in fine powder. Therefore, the crushing during transportation must be avoided as much as possible in order to facilitate transportation and provide methionine of good quality as a product.

In view of the above circumstances, an object of the present invention is to provide a method for transporting airflow of methionine that can minimize the crushing of methionine.

Means to Solve Problems

The present inventors have intensively studied to the prevention of crushing during transportation when airflow of methionine that is a granular material is transported, and as a result, found that the crushing of methionine can be effectively suppressed by controlling the mixing ratio of methionine and carrier gas, and completed the present invention.

On the above-mentioned findings, the present invention encompasses the following embodiments.

The method of airflow transportation of methionine of the first aspect (hereinafter sometimes referred to as "the method of the present invention") is characterized in that when methionine is transported as airflow using carrier gas, the flow state of methionine is a low concentration floating flow type, and the mixing ratio of methionine and carrier gas is in the range of 4 to 10 kg-methionine/kg-carrier gas.

The airflow transportation method for methionine according to the second aspect is characterized in that, in the first aspect, the mixing ratio is in the range of 5 to 10 kg-methionine/kg-carrier gas.

The airflow transportation method for methionine according to the third aspect is characterized in that, in the first or second aspect, the D50 before the transportation of methionine is in the range of 150 to 425 µm.

According to the first aspect of the present application, when the mixing ratio of methionine and carrier gas is 4 to 10 kg-methionine/kg-carrier gas, no clogging is occurred and the increase rate of the fine powder can be suppressed to 1.5% or less.

According to the second aspect of the present application, when the mixing ratio of methionine and carrier gas is 5 to 10 kg-methionine/kg-carrier gas, no clogging is occurred and the increase rate of the fine powder can be suppressed to 1% or less.

According to the third aspect of the present application, if the D50 of methionine is in the range of 150 to 425 µm, the increase rate of the fine powder can be suppressed to 1.5% or less by maintaining the mixing ratio at 4 to 10 kg-methionine/kg-carrier gas, and can be suppressed to 1% or less by maintaining the mixing ratio at 5 to 10 kg-methionine/kg-carrier gas.

BRIEF DESCRIPTION OF DRAWINGS

FIG. 1 indicates a graph which shows the relationship between the mixing ratio and the crushing ratio in an Example.

FIG. 2 indicates a block diagram of the experimental apparatus used for the experiment of an Example.

MODE FOR CARRYING OUT THE INVENTION

Hereinafter, embodiments of the present invention are described with reference to the drawings.

The airflow transportation method of methionine of the present invention is typically applied to methionine production apparatus, and in such a manufacturing facility, the produced and dried methionine is transported to a storage section such as a tank, and is further transported to a filling section in which methionine is weighted and is filled in the container. Also, defective products are transported to the outside in order to discard them.

The transportation path used for these transportations includes a transportation line for the storage unit from the end unit of the manufacturing process to the storage unit, a transportation line for the filling unit from the storage unit to the filling unit, and further a discard line for the disposal unit. Since the transportation line for the storage unit and the transportation line for the filling unit are intended to suppress the crushing of methionine, they are transfer lines that have great significance for the application of the present invention. However, the present invention is also applied to transportation lines other than those exemplified here. Although the present invention can be applied to the discard line, there is no need to apply the methionine transported to the discard line because there is no problem even if the methionine transported to the discard line is crushed.

The configuration of the transport line mainly consists of a pipe and an airflow generating means for flowing an airflow through the pipe.

Examples of the pipe are not particularly limited, but include those made of stainless steel or vinyl chloride resin as a material with a diameter of about 20 mm to 300 mm.

As the length of the pipe, one having a length necessary for each transportation line is used.

The piping shape of the pipe is matched to the plant structure, site shape, etc., and a curved pipe (so-called elbow) is inevitably used, which includes those which is bent in a vertical plane, horizontal plane, or inclined plane.

Examples of the airflow generating means include a pressure blower provided at the start end unit of the transport line, and an intake blower provided at the end unit of the transport line. Either the pressure blower or the intake blower may be used, or both may be used. Also, appropriate apparatus other than the blower, such as a compressor or a vacuum pump, may be used.

Methionine is transported in the above-described airflow transport apparatus. The transported methionine is a dried one, and the methionine after the drying is in the form of powders or particles or a mixed form thereof.

The methionine airflow transportation mode to which the airflow transportation method of the present invention is applied is a low-concentration floating flow shape. The low-concentration floating flow type means a transportation form including a mode in which particles are distributed almost evenly in the cross section inside the tube and flow while floating in the carrier gas, and a mode in which a part of the particles floats, but the remaining parts thereof flows without stagnation while contacting the tube bottom.

In the case of maintaining the above low-concentration floating flow type, the pipe pressure and airflow velocity vary depending on the physical conditions of the transport line, but the pipe pressure is generally 0.05 to 0.19 MPa and the airflow velocity is 20 to 40 m/s. However, the present invention can be applied as long as the transportation form is a low-concentration floating flow type, even if the numerical values of the pressure in the pipe and the airflow velocity described above are out of the numerical ranges.

The D50 of methionine after drying to which the airflow transportation method of the present invention is applied is preferably in the range of 150 to 425 μm. D50 is also called the median diameter, and when the particle size of the powder is classified into two from a certain particle size, the diameter which is defined such that the larger side and the smaller side of the particle size distribution are equivalent on the basis of the particle size.

D50 in the present invention is determined from the particle size distribution measured by a sieving method. The specific operation of the sieving method is as follows.

(1) Stack each sieve on a tray so that the openings are 45 μm, 106 μm, 150 μm, 250 μm, 355 μm, 425 μm, 500 μm, 710 μm, and 850 μm in this order.

(2) Place 20 g of methionine on an 850 μm sieve and shake for 16 minutes using a sieve shaker.

(3) The weight of methionine on the pan and each sieve is measured, the weight percentage with respect to the total of these weights is determined, and the particle size distribution is expressed as an integrated distribution under the sieve.

The carrier gas used for airflow transportation can be arbitrarily selected from air, nitrogen, a mixed gas of nitrogen and air, or the like. In order to suppress the dust explosion, a carrier gas having an oxygen concentration of 16% or less is preferable.

When the airflow transport mode is a low-concentration floating flow type and the above conditions for airflow transport including the above-described D50 value range of methionine is assumed, in the case where the mixing ratio of methionine and carrier gas described below is kept, the crushing ratio of methionine can be effectively suppressed.

The above-described mixing ratio is preferably in the range of 4 to 10 kg-methionine/kg-carrier gas.

As shown in FIG. 1, when the mixing ratio is less than 4, the crushing ratio of methionine during transportation starts to increase, and when it is 3.8 or less, the crushing ratio is increased. When the mixing ratio exceeds 10, the clogging is likely to occur, and when it is 12 or more, the transportation cannot be conducted due to clogging.

Accordingly, when the mixing ratio is in the range of 4 to 10, no clogging occurs and the methionine after drying is hardly crushed, and thereby the crushing ratio can be suppressed to 1.5% or less.

In the present invention, a more preferable range of the mixing ratio is 5 to 10 kg-methionine/kg carrier gas.

When the mixing ratio is 5 to 10, methionine is less likely to be crushed, and the crushing ratio can be suppressed to 1% or less as shown in FIG. 1.

As used herein, the meanings of the terms used are as follows.

The "mixing ratio" is a ratio calculated by the weight ratio of the methionine weight transported per time and the carrier gas (for example, air) discharged from the airflow generating means such as a blower.

The "Crushing" means that the particle size is reduced to 100 μm or less.

The "Crushing ratio (%)" is a ratio calculated by (increase amount of fine powder having a particle size of 100 μm or less after transportation/the total amount of methionine powder before transportation)×100.

EXAMPLES

Next, Examples of the present invention are shown below, but the present invention is not limited thereto.

First, experimental apparatus is described with reference to FIG. 2.

1 is a hopper, 2 is a transport pump for transport line of methionine, 3 is a first receiving tank, and 4 is a second receiving tank. The hopper 1 is charged with methionine. Carrier gas is supplied to the start unit of the transportation line 2. A separator 5 is installed immediately before entering the first receiving tank 3, methionine having a normal particle diameter is dropped into the first receiving tank 3, and methionine pulverized into fine powder is transported to the second receiving tank 4. The gas is released to the atmosphere through the bag filter 6. The transportation pipe 2 constituting the transportation line 2 has an inner diameter of 50 mm, a length of 100 m, and a curved pipe portion having a curvature radius of 450 mm at 10 locations.

The particle size distribution D50 of methionine that is conducted by airflow transportation was in the range of 150 to 425 μm.

In order to suppress the dust explosion, a gas with an oxygen concentration of 16% or less was used as the carrier gas.

The low concentration floating flow shape was maintained by using the apparatus shown in FIG. 2 with a pipe pressure of 0.05 to 0.15 MPa and an airflow velocity of 20 to 40 m/s. Then the airflow transportation test was conducted by changing the mixing ratio of methionine and carrier gas. The particle size of the sample before the transportation, and the sample in the first receiving tank 3 and the second receiving tank 4 after the transportation were measured, and the crushing ratio of 100 μm or less after transportation, that is, the increase ratio of the fine powder was measured. The results are shown in FIG. 1.

In FIG. 1, the horizontal axis is the mixing ratio (unit is kg-methionine/kg-air as carrier gas), and the vertical axis is the crushing ratio (unit is %), that is, the rate of increase of powder particles of 100 μm or less.

From the same figure, when the mixing ratio is between 4 and 10, the crushing ratio (%) shows a small value of 1.5% or less, but when the mixing ratio is below 4, the crushing ratio decreases to about 1.5% as the mixing ratio decreases, and it has been found that the crushing ratio has been increased to over 2%.

It was also found that when the mixing ratio was between 5 and 10, the crushing ratio was less than 1%, and when the mixing ratio was increased from 5 to 10, the crushing ratio was reduced from about 0.8 to about 0.4.

It was found that when the mixing ratio exceeded 12, the clogging is occurred and the transportation could not be performed.

Based on the above experimental results, it was found that the mixing ratio should be about 4 to 10 to suppress the crushing ratio below 1.5%, and about 5 to 10 to suppress it below 1%. It should be noted that the upper limit of the mixing ratio was considered to be 10 because the clogging becomes impossible when the mixing ratio exceeds 10.

Considering the handling properties and quality in the post-process in the production of methionine, it is desirable to keep the crush rate to 1.5% or less, preferably 1% or less. It was found that the airflow transportation method of the present invention is effective in achieving such a low crushing ratio.

INDUSTRIAL APPLICABILITY

The methionine airflow transportation method of the present invention is not limited to a methionine production apparatus, and can be applied without limitation as long as it is a technical field where methionine transportation is required. For example, as such an example, feed production apparatus for adding methionine to livestock feed, livestock breeding apparatus for supplying methionine to feed in livestock breeding grounds, and raw materials for reaction kettles for producing products using methionine as raw materials transfer apparatus etc., may be included.

EXPLANATION OF SYMBOL

1 Hopper
2. Transport pipe
3. First receiving tank
4. Second receiving tank
5. Separator
6. Bag filter

The invention claimed is:

1. A method of airflow transportation of methionine which is characterized in that when methionine is transported as airflow using carrier gas, the flow state of methionine is a low concentration floating flow type, and the mixing ratio of methionine and carrier gas is in the range of 4 to 10 kg-methionine/kg-carrier gas.

2. The method of airflow transportation of methionine according to claim 1 which is characterized in that the mixing ratio is in the range of 5 to 10 kg-methionine/kg-carrier gas.

3. The method of airflow transportation of methionine according to claim 1, which is characterized in that the D50 before the transportation of methionine is in the range of 150 to 425 μm.

4. The method of airflow transportation of methionine according to claim 2, which is characterized in that the D50 before the transportation of methionine is in the range of 150 to 425 μm.

* * * * *